United States Patent [19]

Gaskell et al.

[11] 4,168,777
[45] Sep. 25, 1979

[54] SCALPEL BLADE REMOVER AND COLLECTOR

[75] Inventors: John A. Gaskell, Nunawading; George A. B. Staniland, Upwey, both of Australia

[73] Assignee: Smith and Nephew (Australia) Pty, Ltd., Victoria, Australia

[21] Appl. No.: 899,986

[22] Filed: Apr. 25, 1978

[30] Foreign Application Priority Data

May 27, 1977 [AU] Australia ............... 25594/77

[51] Int. Cl.$^2$ .................. B65D 25/00; B65F 7/00; A61B 19/02; A61F 13/00
[52] U.S. Cl. ................................. 206/359; 206/370
[58] Field of Search ............... 206/359, 370, 205, 366, 206/438, 354; 30/40.2; 221/63

[56] References Cited

U.S. PATENT DOCUMENTS

| 1,476,401 | 12/1923 | Hechmer | 221/63 |
|---|---|---|---|
| 2,643,452 | 6/1953 | Fennelly | 30/40.2 |
| 2,741,838 | 4/1956 | Breazeale | 30/40.2 |
| 3,244,317 | 4/1966 | Raybin | 206/370 |
| 3,834,018 | 9/1974 | Dawidowicz et al. | 206/359 |
| 3,876,067 | 4/1975 | Schwarz | 206/366 |
| 4,106,620 | 8/1978 | Brimmer et al. | 206/359 |
| 4,120,397 | 10/1978 | Neumann | 206/370 |

Primary Examiner—William T. Dixson, Jr.
Attorney, Agent, or Firm—Thomas W. Cole

[57] ABSTRACT

A device for removing and storing the blade of a scalpel of the type comprising a handle having a reduced section at one end thereof with an elongated boss on one side of said reduced section, said boss having a recess partially extending along each side thereof, and a blade having an elongated slot therein with a reduced section, said slot being complemental to said recessed boss, such that the blade is retained on said boss when the reduced section of the blade slot engages the recess on the boss, comprises a container adapted to accommodate at least one blade, an aperture in said container shaped to allow the introduction of the blade retaining end of the scalpel into said container, abutment means projecting outwardly from said aperture adapted to abut against the inner end of the blade when the handle is removed from said container restraining the blade from outward movement thereof and allowing retention of the blade in the container.

7 Claims, 4 Drawing Figures

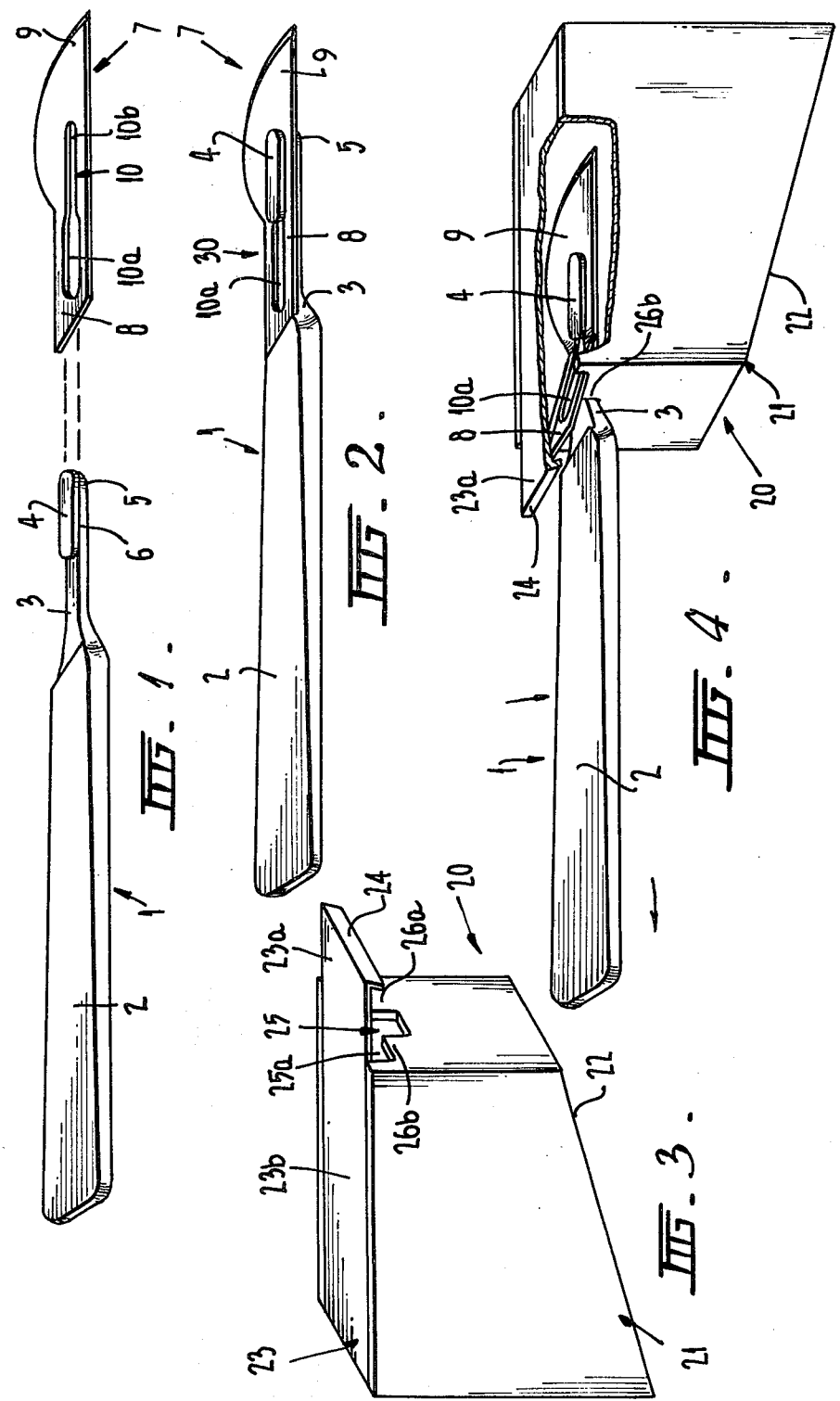

SCALPEL BLADE REMOVER AND COLLECTOR

This invention relates to scalpels (or surgical knives) of the type comprising a handle having a reduced section at one end thereof with an elongated boss on one side of said reduced section, said boss having a recess partially extending along each side thereof, and a blade having an elongated slot therein with a reduced section, said slot being complemental to said recessed boss, such that the blade is retained on said boss when the reduced section of the blade slot engages the recess on the boss.

The traditional scalpel (surgical knife) has been extensively used in surgery for a number of years and would be the most widely used surgical instrument in the world at present.

The scalpel, due to its extensive use in all parts of the world, consists of a standardised range of handles and blades.

It is generally accepted that the handle section of the scalpel, due to its expense, is cleaned, sterilized and re-used after each surgical procedure, while the blade section is used once only thereby ensuring the sharpness of the blade each time it is used.

Due to the critical conditions under which scalpels are used it is necessary to replace the blade fairly often and quickly. At present this is difficult to accomplish due to the blade being firmly locked onto the handle, the danger involved in attempting to manipulate a fairly sharp, small and contaminated blade using fingers which may be accidentally cut and infected. There is a further problem in storing and transporting used scalpel blades to a point of disposal.

The generally used present procedure is to remove the blade from the handle using forceps or similar device and placing the used blades in a container for transport to a disposal station. It is subsequently necessary to clean and sterilize the contaminated forceps and transport container.

Accordingly, it is the principal objective of the present invention to provide a device for removing the blade from the scalpel handle, said device being simple and economical to manufacture, capable of easily and safely removing the blade and storing one or more of said blades and being disposable at the same point as the blades.

Accordingly, the present invention provides a device for removing and storing the blade of a scalpel of the type described hereinabove comprising a container adapted to accommodate at least one blade, an aperture in said container shaped to allow the introduction of the blade retaining end of he scalpel into said container, abutment means projecting outwardly from said aperture adapted to abut against the inner end of the blade when the handle is removed from said container restraining the blade from outward movement thereof and allowing retention of the blade in the container.

Advantageously, the above device also comprises means associated with the container restraining movement of the blade supporting end of the scalpel in a direction opposite to the pressure applied to the scalpel handle prior to withdrawal of the scalpel from the container. The restraining means may take the form of a flat portion of the container extending from the aperture where the abutment means is an extension of the flat portion and has a lip extending from the extension for the purpose of abutting and restraining the blade when the blade is removed. Advantageously, the above lip extends from the outer extremity of the extended flat portion.

Conveniently, from the point of view of manufacture of the device, the flat portion of the container is integrally moulded with the container from a suitable synthetic plastic material.

Accordingly to another embodiment of the invention, the flat portion serves as a lid for the container and the lid material may either be the same as the container or different.

Advantageously, the flat portion of the container is partially unattached to the container in order to allow deflection of the flat portion when the blade supporting end of the scalpel is inserted into the container aperture.

The invention will now be described with reference to a preferred practical arrangement shown in the accompanying drawings wherein:

FIG. 1 shows a typical scalpel handle and complemental blade before assembly;

FIG. 2 shows the assembled scalpel with the blade located on the reduced section of the scalpel handle;

FIG. 3 shows a device for removal and storage of scalpel blades according to this invention; and FIG. 4 shows the device of FIG. 3 in use for the removal of the blade from the scalpel.

Referring to FIGS. 1 and 2, a scalpel handle generally indicated as 1 consists of a main section 2 and a reduced section 3 having a raised elongated boss 4 thereon coextensive with the end 5 of the reduced section as shown. The boss 4 has a recess 6 partially extending along both sides of the boss from its extremity 5.

A scalpel blade, generally indicated as 7, has a rectangular portion 8, a curved portion 9 and an elongated slot 10 having a section 10a and a reduced section 10b. The slot section 10a is adapted for complemental engagement with boss 4 and the reduced section 10b is adapted for location in the recesses 6, such that locked assembly of the scalpel blade 7 and handle occurs when the slot section 10a of the blade is superimposed on boss 4 and the blade is moved towards the handle section 2 (FIG. 2), the inter-engagement of recess 6 and reduced slot 10b locking the blade 7 relative to the blade handle 1.

Referring to FIGS. 3 and 4, the device of the invention, generally indicated as 20, consists of a container 21 having a sloping base 22 and a flat rectangular lid 23 which can either be integral with or separate from the container 21 (see FIG. 3).

The lid 23 has an outward projection 23a with a downwardly turned lip 24 and may advantageously have a portion 23b unconnected with the container.

The container 21 has an aperture, generally indicated as 25 on its front face designed to permit entry into the container of the blade supporting section of the scalpel (indicated as 30, FIG. 2), i.e. the reduced section 3 with the blade 7 supported on boss 4. The aperture 25 has a wide section 25a designed to permit the passage therethrough of the blade 7 and a narrow lower section 25b for the passage therethrough of the reduced section 3 (including boss 4) of the handle 1. Aperture sections 25a and 25b are joined at shoulders 26a and 26b.

In use, the contaminated blade supporting section 30 of a scalpel, as shown in FIG. 2, is inserted into the aperture 25 to an extent such that the inner end of the blade 7 is somewhat inward of the lip 24, the reduced section 3 of the scalpel handle and blade 7 located respectively in aperture sections 25b and 25a respectively. The scalpel handle may then be subjected to appropriate downward pressure causing the inner end of the blade 7 to rise and abut against the inner surface of the lip 24. It will be appreciated that the shoulders 26a and 26b act as pivotal points when the scalpel handle is depressed. This rise of the inner end of blade 7 is caused by the latter being restrained from moving upwardly responsive to downward pressure on scalpel handle 2 by the flat lid 23 extending inwardly from the top of the aperture 25 or by the depression of the reduced end 3 of the scalpel to the base of the lower aperture section 25b as a result of downward pressure on the scalpel handle 2 whereby the inner end of the blade 7 is lifted at shoulders 26a and 26b, depending on the size and configuration of the aperture 25 particularly the lower section 25b. By moving upwardly, the inner end of the blade 7 rises to the level of the lid projection 23a and when the scalpel is then withdrawn from the container in the direction shown (FIG. 4) the blade 7 is removed from the boss 4 by means of the reduced slot 10b sliding out of engagement with the recess 6 of the boss 4. As the scalpel handle is removed the blade 7 drops to the base 22 of the container and the sloping base assists in the stacking of the blade.

When the container is filled with used contaminated blades, the container (and blades) may suitably be disposed of.

It will be appreciated that the device may be constructed such that, for instance, it is wall mounted and that the container 21 constitutes a separate unit from the unit comprising the aperture 25 and lid 23 so that when the container 21 is filled with blades, it can simply be removed from the rest of the device and separately disposed of.

We claim:

1. A device for removing and storing the blade of a scalpel of the type having a blade retaining reduced section at one end and a handle at the other end comprising:
   (a) a container for accomodating at least one blade,
   (b) an aperture in said container shaped to allow the insertion of said blade retaining reduced section of said scalpel into said container and the separation of the inner end of said blade from said section;
   (c) a restraining means in said container for restraining the movement of said blade inside said container and causing said inner end of said blade to separate from said reduced section of said scalpel when said handle of said scalpel is depressed, and
   (d) an abutment means on said container projecting outwardly from said aperture for abutting against said inner end of said blade and retaining said blade within said container when said blade retaining reduced section is withdrawn from said container after said scalpel handle is depressed.

2. A device as claimed in claim 1, wherein said restraining means includes a wall of said container and said abutment means includes an extention of said wall projecting outwardly from said aperture having a lip for abutting against said inner end of said blade and retaining said blade within said container.

3. A device as claimed in claim 2, wherein said lip extends from the outer extremity of said extention of said wall.

4. A device as claimed in claim 2, wherein said wall of said container is integrally molded with said container from a suitable synthetic plastic material.

5. A device as claimed in claim 2, wherein said wall serves as a lid for said container.

6. A device as claimed in claim 2, wherein said wall is partially unattached to said container to allow deflection of said wall when said blade retaining end of said scalpel is inserted into said container aperture.

7. A device for removing and storing the blade of a scalpel of the type having a reduced section at one end for slidably engaging and disengaging a scalpel blade, and a handle at the other end, comprising:
   (a) a container for receiving and storing at least one scalpel blade;
   (b) a side wall in said container having:
      (i) an aperture for receiving said reduced section of said scalpel and for providing a pivot point in said wall when said reduced section of said scalpel is inserted into said aperture and said handle of said scalpel is depressed, and
      (ii) a slot adjoining said aperture of lesser width than said scalpel blade but of greater width than said reduced section of said scalpel for receiving said reduced section when said reduced section is inserted into and pivoted about said aperture when said scalpel handle is depressed,
   (c) a top wall in said container abutting said side wall and adjacent to said aperture for causing the bottom edge of said scalpel blade to spread apart from said reduced section of said scalpel by exerting a counter-force on the end of said scalpel blade when said reduced section is inserted into and pivoted about said aperture by depressing said handle of said scalpel, and
   (d) a lip means extending from said top wall of said container and adjacent to said aperture for receiving said bottom edge of said scalpel blade when said scalpel is withdrawn after said reduced section of said scalpel has been inserted through and pivoted about said aperture,
   whereby said scalpel blade is slidably disengaged from said scalpel handle.

* * * * *